United States Patent
Kaito et al.

(10) Patent No.: US 6,485,642 B2
(45) Date of Patent: Nov. 26, 2002

(54) LIQUID CHROMATOGRAPH

(75) Inventors: Katsuaki Kaito, Nagaokakyo (JP); Yosuke Iwata, Kyoto (JP); Kaoru Murata, Tsukuba (JP); Naoki Asakawa, Tsukuba (JP)

(73) Assignees: Shimadzu Corporation, Kyoto (JP); Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/873,411

(22) Filed: Jun. 5, 2001

(65) Prior Publication Data

US 2002/0011437 A1 Jan. 31, 2002

(30) Foreign Application Priority Data

Jun. 5, 2000 (JP) .................................... 2000-167293

(51) Int. Cl.⁷ .............................................. B01D 15/08
(52) U.S. Cl. .................... 210/198.2; 210/656; 210/659; 210/101
(58) Field of Search .............................. 210/635, 656, 210/659, 198.2, 101, 143

(56) References Cited

U.S. PATENT DOCUMENTS

| | | | | |
|---|---|---|---|---|
| 5,135,718 A | * | 8/1992 | Kawaguchi | 210/198.2 |
| 5,158,675 A | * | 10/1992 | Allington | 210/198.2 |
| 5,468,643 A | * | 11/1995 | Su | 210/198.2 |
| 5,630,943 A | * | 5/1997 | Grill | 210/198.2 |
| 5,744,029 A | * | 4/1998 | Li | 210/198.2 |
| 5,852,231 A | * | 12/1998 | Kaji | 210/198.2 |
| 5,935,443 A | * | 8/1999 | Anderson | 210/198.2 |
| 5,958,227 A | * | 9/1999 | Uematsu | 210/198.2 |
| 5,968,361 A | * | 10/1999 | Goetzinger | 210/198.2 |
| 6,149,816 A | * | 11/2000 | Quinn | 210/198.2 |
| 6,235,197 B1 | * | 5/2001 | Anderson | 210/198.2 |
| 6,344,172 B1 | * | 2/2002 | Afeyan | 210/198.2 |
| 6,365,050 B1 | * | 4/2002 | Cauchon | 210/198.2 |
| 6,402,947 B1 | * | 6/2002 | Altamirano | 210/198.2 |

* cited by examiner

*Primary Examiner*—Ernest G. Therkorn
(74) *Attorney, Agent, or Firm*—Radar, Fishman & Grauer PLLC

(57) ABSTRACT

A sample solution is sent into a concentration column through a three-way joint and a three-way switching valve to trap and concentrate the sample components on the concentration column, followed by injecting the sample solution into an injector by operating a first dilution solvent pump. When a large volume of the sample solution is to be sent or when the sample solution has a high solvent strength, trapping and concentration on the concentration column may be facilitated by replacing the sample solvent with a second dilution solvent by allowing the second dilution solvent to flow into the three-way joint after setting the flow rate of the second dilution solvent from a second dilution solvent vessel to a prescribed flow rate using a second dilution solvent pump.

4 Claims, 2 Drawing Sheets

LIQUID CHROMATOGRAPH

BACKGROUND OF THE INVENTION

1. Field of the Invention

The present invention relates to a liquid chromatograph.

2. Description of the Related Art

A Liquid chromatograph involves little qualitative information. Accordingly, eluted components have been fractionated and subjected to qualitative analysis using other analytical instruments after optionally concentrating the eluate for correct identification and recognition of sample components.

While an analytical method in which the liquid chromatograph is used with on-line connection to another analytical instrument, such as a mass spectrometer, has been employed, most of the eluate has been split and discharged because the volume to be introduced into the other analytical instruments is limited. While a micro-liquid chromatograph using a column with a column inner diameter of 1 mm or less is effective for reducing the consumed solvent volume, a precise injection of the solvent with an injection volume of as small as 1 microliter or less is required.

However, it costs much labor for the liquid chromatograph to fractionate eluted components and inject them into a qualitative instrument, besides involving a risk of denaturation and loss of the sample components during the concentration process as well as mingling of foreign substances.

In addition, splitting of the eluate for on-line connection of the liquid chromatograph to another instrument such as the mass spectrometer may adversely affect quantitative analysis and sensitivity, although this method is effective for the analysis by the mass spectrometer.

Since the injected solution should form a band as narrow as possible for attaining high resolution among the chromatographic peaks, a large volume of the sample solution cannot be injected even when the sample concentration is low.

SUMMARY OF THE INVENTION

It is an object of the present invention to provide a liquid chromatograph that is able to assay a sample after concentrating the sample solution containing low concentration of components.

The present invention provides a liquid chromatograph comprising a first solvent flow line for diluting a sample solution with a first dilution solvent pump via an injector and for sending the diluted sample solution, and an analytical line for flowing an elution solvent into a flow passageway connecting through an analytical column to a detector using a solvent pump. The first solvent flow line and the analytical line are connected to a switching valve, respectively. The switching valve comprises a concentration column, the concentration column being freely connected to the first solvent flow line and analytical line by switching the switching valve. A second solvent flow line for sending a dilution solvent with a second dilution solvent pump is connected by providing a joint between the injector and switching valve. The sample solution as used herein refers to a solution containing a sample.

In order to omit off-line fractionation and concentration processes that involve much labor, a micro-liquid chromatograph that enables the volume of split solvent to be reduced is utilized with on-line connection to another analytical instrument such as a mass spectrometer, wherein injection of a large volume of low concentration sample solution is enabled by providing a sample concentration step.

In addition, the mixing ratio between the solvents from the first dilution solvent pump and the second dilution solvent pump at the joint may be adjusted by controlling the flow rates of the first and second dilution solvent pumps, enabling the degree of dilution of the sample solution to be freely determined.

It is known in the liquid chromatograph that the solvent used for the sample solution may affect separation of the sample components. Therefore, the volume and composition of the injected solvent introduced into the analytical line should be modified to the preferable composition of the solvent upon analysis using the liquid chromatograph. Appropriate analytical conditions may be employed in the liquid chromatograph according to the present invention, because the solvent for the sample to be trapped on the concentration column, i.e., the solvent to be introduced into the analytical line, can be diluted or substituted with the dilution solution.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

At least one of the first solvent flow line and the second solvent flow line preferably comprises an elimination column through which only a washing solvent flows or through which a mixed solvent of the washing solvent and a dilution solvent flows, and a flow passageway for discharging the washing solvent or the mixed solvent into a drain. As a result, impurities in the dilution solution may be prevented from flowing into the analytical line.

The first and second solvent pumps preferably send different dilution solutions with each other. As a result, adjustment of a reagent solvent including pH adjustment, mixing of an ion pair reagent and adjustment of ionic strength is effected with the dilution solvent from the second dilution solvent pump, allowing trapping mode on the concentration column to be flexible.

Details of the present invention shall now be described hereinafter with reference to FIG. 1.

Figure 1:
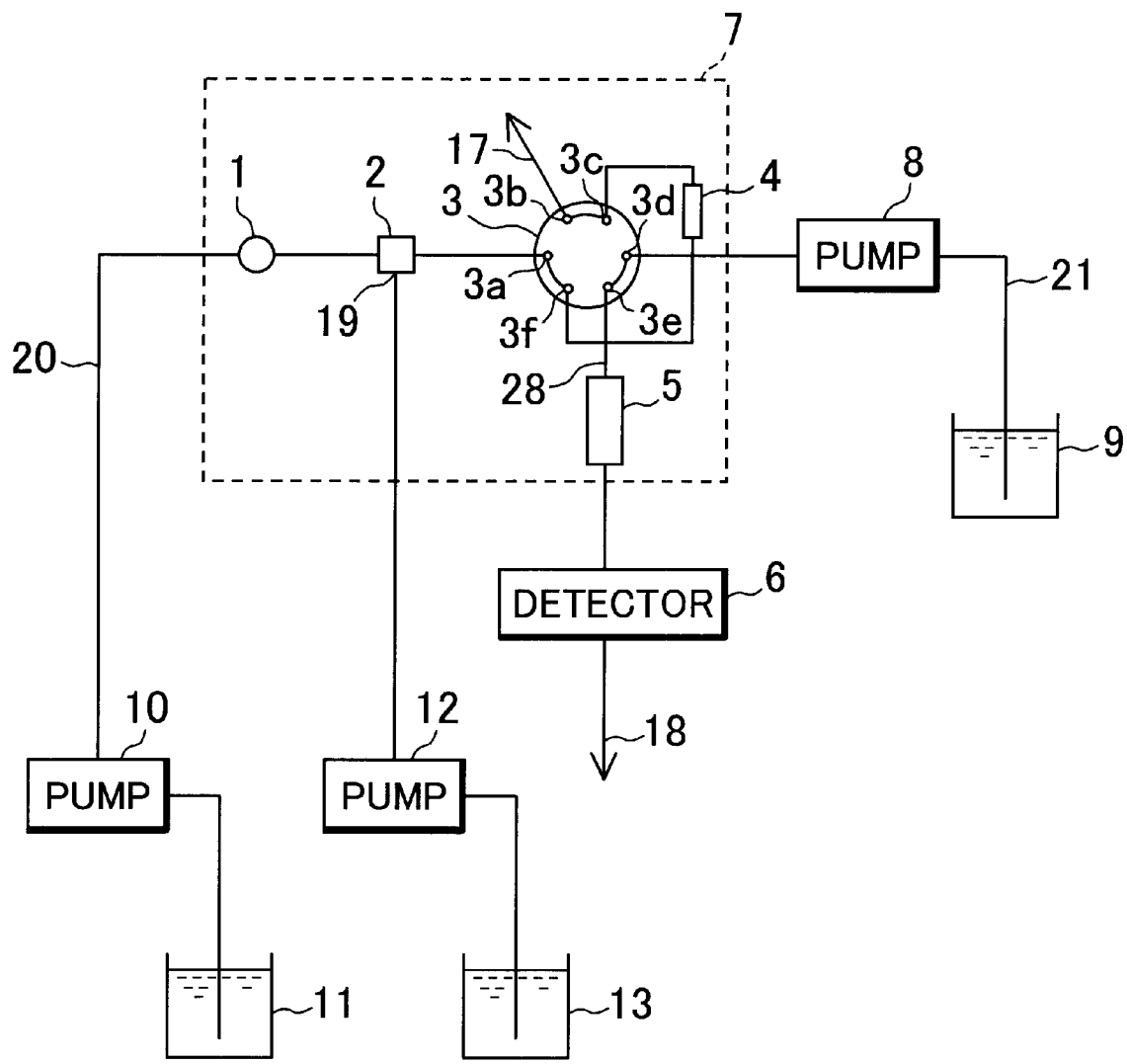
FIG. 1 is a diagram showing a flow passageway in one embodiment of the present invention.

In FIG. 1, the reference numeral 1 denotes an injector, which is connected to a switching port 3a of a six-way switching valve 3 via a three-way joint 2. The reference numeral 4 denotes a concentration column whose both ends are connected to switching ports 3c and 3f of the six-way switching valve 3, respectively. The reference numeral 5 denotes an analytical column, one end of which is connected to a switching port 3e of the six-way switching valve 3 and the other end of which is connected to a detector 6 to construct an analytical line 28.

The injector 1, the three-way joint 2, the six-way switching valve 3, the concentration column 4 and the analytical column 5 are housed in an oven 7. The reference numeral 8 denotes a solvent pump, and the suction side of which is connected to a elution solution vessel 9 containing an elution solvent while the discharge side of which is connected to a switching port 3d of the switching valve 3. These members comprise an elution system 21.

The reference numeral 10 denotes a solvent pump (a first dilution solvent pump) of which it's suction side is connected to a dilution solvent vessel 11 containing a dilution and transfer liquid (referred to as a dilution solvent hereinafter) while it's discharge side is connected to the injector 1. A solvent flow line 20 is composed of these members. The reference numeral 12 denotes another solvent pump (a second dilution solvent pump) of which it's suction side is connected to a dilution solvent vessel 13 containing a dilution solvent while it's discharge side is connected to the three-way joint 2. The reference numerals 17 and 18 denote drains, wherein the drain 17 is connected to the six-way switching valve 3 and the drain 18 is connected to the detector 6.

The method for using the liquid chromatograph and operation thereof shall now then be described hereinafter. The switching ports 3a, 3b and 3d are connected to the switching ports 3f, 3c and 3e, respectively, in the six-way switching valve 3. The flow rate of the dilution solvent vessel 13 is zero.

The dilution solvent is sent from the dilution solvent vessel 11 to the injector 1 through the solvent pump 10 by operating the solvent pump 10. The sample solution injected into the injector 1 is conveyed with the dilution solvent to the six-way switching valve 3 through the three-way joint 2. Since the switching ports 3a and 3f of the six-way switching valve 3 are connected to one another, the sample solution is sent into the concentration column 4 with the dilution solvent. The sample components are trapped with concentration on the concentration column 4 depending on the action of the column packing material. The dilution solvent after passing through the concentration column 4 returns from the switching port 3c into the switching valve 3, and is discharged from the drain 17 through the switching port 3b.

On the other hand, by operation of a solvent pump 8, the elution solvent flows from the elution solvent vessel 9 successively through the six-way switching valve 3, switching ports 3d and 3e, analytical column 5 and detector 6, and is discharged from the drain 18.

Subsequently, the dilution solution fed through the three-way joint 2, by connecting the switching ports 3a, 3c and 3e to the connection ports 3b, 3d and 3f, respectively, by switching the six-way valve 3, is discharged to the drain 17 through the switching ports 3a and 3b. On the other hand, the elution solvent from the solvent pump 8 enters into the concentration column 4 through the switching ports 3d and 3c, elutes the sample components trapped and concentrated on the concentration column 4 out of the column, and enters into the analytical column 5 through the switching ports 3f and 3e. The sample components are separated with each other in the analytical column 5, and sequentially detected with the detector 6.

The process above allows each sample component to be assayed after concentrating in the concentration column 4, even when the sample solution contains low concentration of each component.

When a large volume of the sample solution is to be injected, or when the solvent strength of the sample solution in which sample components are dissolved is high in this example, the flow rate of the dilution solvent from the dilution solvent vessel 13 is adjusted to a prescribed flow rate by operating the solvent pump 12 shown in FIG. 1 to allow the dilution solvent to flow into the three-way joint 2 through its connection port 19. Then, the sample solution is diluted in the three-way joint 2, if the flow rate of the dilution solvent from the dilution solvent vessel 13 is larger than the flow rate of the dilution solvent flowing from the injector 1 together with the sample solution. In other words, the solvent of the sample can be replaced with the dilution solvent, thereby facilitating the sample components to be trapped and concentrated on the concentration column 4.

The mixing ratio between the sample solution flowing from the dilution solvent pump 10 and the dilution solvent flowing from the dilution solvent pump 12 at the three-way joint 2 may be adjusted by controlling the flow rates of the dilution solvent pumps 10 and 12, thereby enabling the dilution ratio of the sample solution to be freely determined.

For example, when a dilution solvent having a high solvent strength is filled in the dilution solvent vessel 11 for preventing the sample components from remaining in the flow passageway, the dilution solvent filled in the dilution solvent vessel 13 is made to have a low solvent strength. The proportion of the dilution solvent sent from the solvent pump 12 is adjusted to be larger than the proportion of the dilution solvent sent from the solvent pump 10 at the three-way joint 2, thereby enabling to reduce adverse effect of the dilution solvent filled in the dilution solvent vessel 11 on trapping of the sample components on the concentration column 4.

Also, the concentration column may be endowed with flexible trapping modes by permitting the dilution solvent filled in the dilution solvent vessel 13 to have such functions as adjusting pH of the reagent solvent, mixing of ion-pair reagents and adjusting the ionic strength of the solvent.

Figure 2:
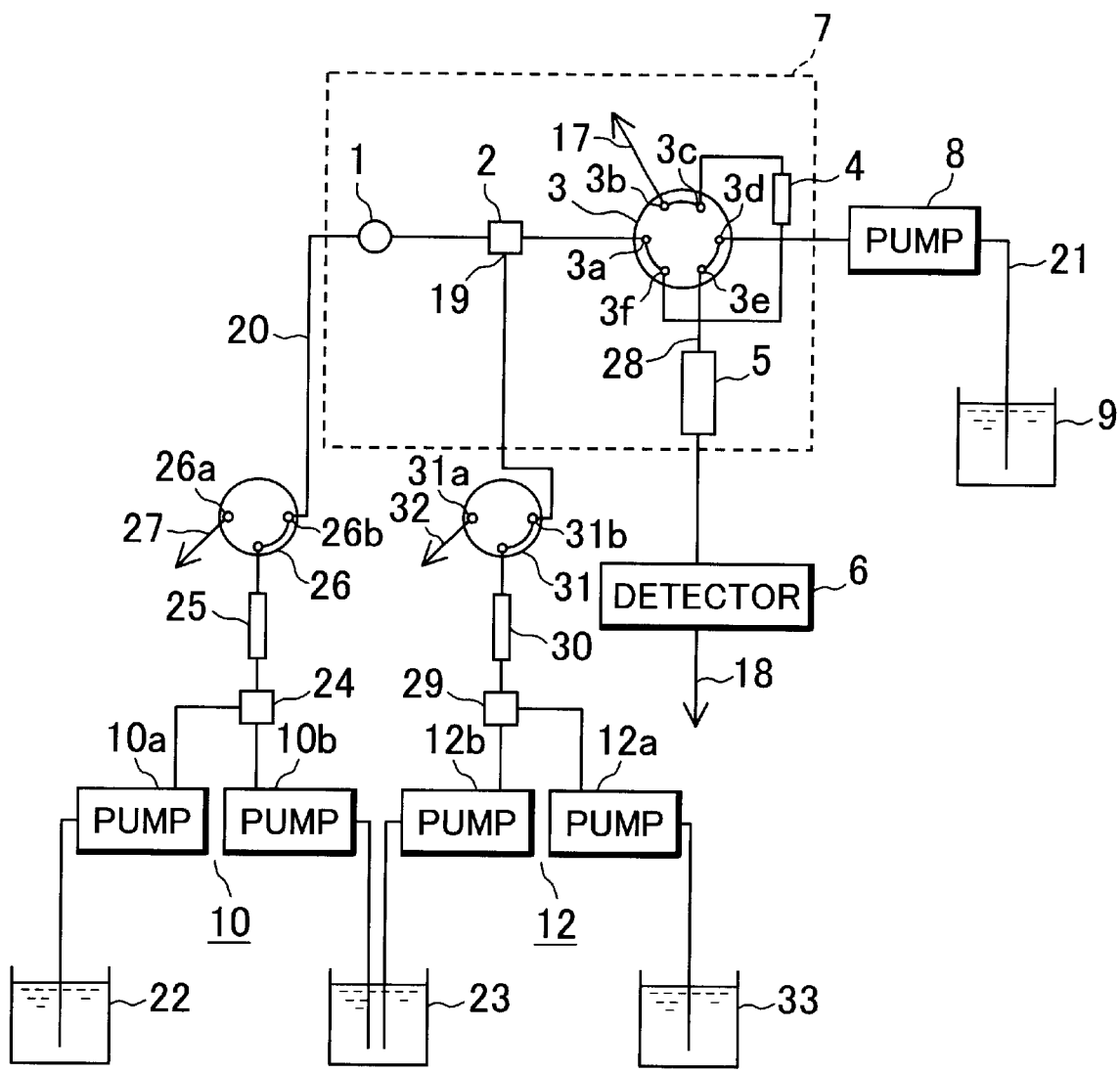
FIG. 2 is a diagram showing a flow passageway in another embodiment of the present invention.

The example in which an instrument for eliminating impurities in the dilution solvent is integrated into the mechanism described above shall now be described below with reference to FIG. 2.

Two solvent pumps 10a and 10b are used in place of the solvent pump 10 in FIG. 1. One of the solvent pumps 10a is connected to a dilution solvent vessel 22 while the other solvent pump 10b is connected to a cleaning solvent vessel 23. Both solvent pumps 10a and 10b are connected to an elimination column 25 through, or without passing through, a mixer 24. The solvent pumps 10a and 10b may be connected to the dilution solvent vessel 22 and cleaning solvent vessel 23, respectively, by simply inserting their suction tubes into respective solvents. The elimination column 25 is connected to a three-way switching valve 26, which provides a switching port 26a to a drain 27 and a switching port 26b to a solvent flow line 20.

Two solvent pumps 12a and 12b are also used in place of the solvent pump 12 in FIG. 1. One of the pumps 12a is connected to a dilution solvent vessel 33 while the other solvent pump 12b is connected to the cleaning solvent vessel 23. Both solvent pumps 12a and 12b are connected to an elimination column 30 through, or without passing through, a mixer 29. The solvent pumps 12a and 12b may be connected to the dilution solvent vessel 33 and cleaning solvent vessel 23, respectively, by simply inserting their suction tubes into respective solvents. The elimination column 30 is connected to a three-way switching valve 31, which provides a switching port 31a to a drain 32 and a switching port 31b to a three-way joint 2.

The elimination columns 25 and 30 are able to temporarily adsorb impurities, or to remove impurities.

The operation of the system in the example shown in FIG. 2 shall now be described hereinafter. The solvent pumps 10a and 12a are operated for sending the dilution solvents to the elimination columns 25 and 30. Impurities in the dilution solvents are temporarily adsorbed on or removed by the elimination columns. The cleaned dilution solvents are then sent to the solvent flow line 20.

When the elimination columns 25 and 30 are saturated with impurities, the solvent pumps 10a and 12a are halted, and the three-way switching valve 26 is switched to connect to the drain 27 through the switching port 26a, and the three-way switching valve 31 is switched to connect to the drain 32 through the switching port 31a. The solvent pumps 10b and 12b are allowed to operate thereafter to send the cleaning solvent to the elimination columns 25 and 30. The impurities temporarily adsorbed or removed are washed out, and are discharged to the drains 27 and 32.

A mixed solvent of the cleaning solvent and dilution solvent in an appropriate mixing ratio may be used for cleaning the elimination column. The solvent pumps 10a, 10b, 12a and 12b suck the cleaning solvent and dilution solvent in an appropriate mixing ratio by controlling the flow rate of each pump, or by controlling the flow rates to the mixers 24 and 29. The resultant mixed solvent is sent to the elimination columns 25 and 30 for cleaning them.

The procedures above enable the impurities in the dilution solution to be prevented from entering into the analytical line 28. Consequently, impurity peaks are prevented from appearing and sample component peaks become clear, thereby enabling reproducibility of quantitative assay to be excellent.

While cleaning of the elimination columns 25 and 30 have been simultaneously carried out, they may be separately cleaned. One solvent pump may be used in place of the solvent pumps 10 and 12 respectively by providing a switching valve that enables selection of the dilution solvent and leaning solvent.

It is possible to improve reproducibility by warming the system with a column oven 7 for respective operations described above.

Although use of a resistive tube may be contemplated for controlling the flow rate, the inner diameter of the tube of the analytical line is not required to be smaller than the inner diameter of the tube inherently required for the analysis since no resistive tubes are used in the present invention. Accordingly, a stable and continuous analytical operation is made possible without causing any troubles because accumulation of impurities ascribed to dilution can be avoided.

While the dilution solvent vessels are provided for the solvent pumps 10 and 12, respectively, a common dilution solvent vessel may be provided for the solvent pumps 10 and 12.

The liquid chromatograph according to the present invention may be used, for example, for deciding whether the concentrations of residual chemicals in ethanol are below an acceptable range or not after cleaning an apparatus for manufacturing a medicine has been washed with ethanol. Although conventionally the concentration has been quantified with a liquid chromatograph after evaporating discharged ethanol using an evaporator, the concentration process required a long period of time. In the liquid chromatograph according to the present invention, on the contrary, discharged ethanol may be directly introduced into the system as a sample solution and measured, thereby enabling the time for pretreatment to be shortened.

The liquid chromatograph according to the present invention may also be used for studying pharmacokinetics by measuring the concentration of drugs and metabolic products in the blood. Normally, it has been inevitable to remove serum proteins using an organic solvent such as acetonitrile and ethanol for measuring the drugs and metabolic products in the blood with the liquid chromatograph. Since it has been impossible in the conventional liquid chromatograph to inject a large volume of an organic solvent as a sample solution, the sample solution should be evaporated to dryness followed by dissolving the residue again in water to inject into the liquid chromatograph. On the contrary, since the sample solution may be diluted in the liquid chromatograph according to the present invention, the sample solution in an organic solvent may be directly used for the analysis to enable the time for pretreatment to be reduced.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A liquid chromatograph comprising:

a first solvent flow line comprising an injector for injecting a sample solution, the sample solution injected from the injector being diluted by sending a dilution solvent from a first dilution solvent pump;

an analytical line for flowing an elution solvent into a flow passageway connecting through an analytical column to a detector using a solvent pump;

a switching valve comprising a concentration column, for switching a flow passage of the concentration column to connect to the first solvent flow line and analytical line; and a second solvent flow line connected between the injector and switching valve for flowing a dilution solvent with a second dilution solvent pump.

2. A liquid chromatograph according to claim 1, wherein at least one of the first solvent flow line and the second solvent flow line comprises an elimination column for eliminating impurities in the dilution solution, and the elimination column comprises a flow passageway for sending only a washing solvent or for sending the washing solvent by mixing with the dilution solution followed by discharging the solvent to a drain.

3. A liquid chromatograph according to claim 1, wherein the first dilution solvent pump can send a dilution solvent different from the dilution solvent sent with the second dilution solvent pump.

4. A liquid chromatograph according to claim 1, wherein at least the injector, analytical column and concentration column are housed in an oven to control their temperature.

* * * * *